United States Patent [19]

Hedge

[11] B 4,014,949

[45] * Mar. 29, 1977

[54] SEPARATION OF CYCLIC COMPOUNDS WITH MOLECULAR SIEVE ADSORBENT

[75] Inventor: John A. Hedge, Wilmington, Del.

[73] Assignee: Sun Ventures, Inc., St. Davids, Pa.

[ * ] Notice: The portion of the term of this patent subsequent to June 6, 1989, has been disclaimed.

[22] Filed: Dec. 19, 1973

[21] Appl. No.: 426,274

[44] Published under the second Trial Voluntary Protest Program on January 20, 1976 as document No. B 426,274.

Related U.S. Application Data

[60] Division of Ser. No. 263,372, June 6, 1962, Pat. No. 3,840,610, which is a continuation-in-part of Ser. No. 7,273, Jan. 30, 1970, Pat. No. 3,668,267, and a continuation-in-part of Ser. No. 207,870, Dec. 14, 1971, and a continuation-in-part of Ser. No. 256,863, May 25, 1972, Pat. No. 3,772,399.

[52] U.S. Cl. .................. 260/674 SA; 208/310 Z
[51] Int. Cl.² .......................................... C07C 7/13
[58] Field of Search ......... 260/674 SA, 666 P, 675; 208/310, 310 Z

[56] References Cited

UNITED STATES PATENTS

| | | | |
|---|---|---|---|
| 2,988,503 | 6/1961 | Milton et al. | 260/666 |
| 3,126,425 | 3/1964 | Eberly et al. | 260/674 |
| 3,130,007 | 4/1964 | Breck | 252/455 |
| 3,485,748 | 12/1969 | Eberly et al. | 208/310 |
| 3,558,730 | 1/1971 | Neuzil | 260/674 |
| 3,626,020 | 12/1971 | Neuzil | 260/674 |
| 3,663,638 | 5/1972 | Neuzil | 260/674 |
| 3,665,046 | 5/1972 | Rosset | 260/674 |
| 3,668,266 | 6/1972 | Chen et al. | 260/674 |
| 3,668,267 | 6/1972 | Hedge | 260/674 |
| 3,686,343 | 8/1972 | Bearden et al. | 260/674 |
| 3,699,182 | 10/1972 | Cattanach | 260/674 |
| 3,734,974 | 5/1973 | Neuzil | 260/674 |
| 3,840,610 | 10/1974 | Hedge | 260/674 |

FOREIGN PATENTS OR APPLICATIONS 734,798  12/1969  Belgium .................. 260/674 SA

*Primary Examiner*—Delbert E. Gantz
*Assistant Examiner*—C. E. Spresser
*Attorney, Agent, or Firm*—J. Edward Hess; Donald R. Johnson; Stanford M. Back

[57] ABSTRACT

Selective adsorption of one cyclic compound from a fluid mixture with a structurally similar cyclic compound can be obtained with molecular sieves (crystalline aluminosilicate zeolites) which have been partially dehydrated at a temperature in the range of 80°–300°C. Preferably the Al/Si ratio in the zeolite framework is in the range of 0.2–0.65. For example, m-xylene can be separated from p-xylene by selective adsorption of the m-xylene on NaY zeolite which was partially dehydrated at 125° C. and contains about 12 wt % water by ignition analysis.

5 Claims, No Drawings

4,014,949

SEPARATION OF CYCLIC COMPOUNDS WITH MOLECULAR SIEVE ADSORBENT

CROSS REFERENCE TO RELATED APPLICATIONS

This application is a division of my application Ser. No. 263,372 filed June 6, 1972 (now U.S. Pat. No. 3,840,610, issued Oct. 8, 1974) which is a continuation-in-part of my applications Ser. No. 7,273, filed Jan. 30, 1970, patented on June 6, 1972 as U.S. Pat. No. 3,668,267; Ser. No. 207,870, filed Dec. 14, 1971 and Ser. No. 256,863, filed May 25, 1972 (now U.S. Pat. No. 3,772,399, issued Nov. 13, 1973), the entire disclosure of which are hereby incorporated herein by this reference.

Other relevant patents and applications (which show zeolites which can be used as adsorbents in the present invention, or show methods of isomerization or other conversions of dimethylnaphthalenes) are Ser. No. 716,190, filed Mar. 26, 1968 and Ser. No. 211,040, filed Dec. 22, 1971 (now U.S. Pat. No. 3,839,228 issued Oct. 1, 1974), both of Kirsch, Barmby and Potts (which disclose polyvalent metal exchanged zeolites and methods for activation thereof); U.S. Pat. No. 3,244,758, patented Apr. 5, 1966 of Eberhardt, which shows the preparation of 1,5-dimethylnaphthalene from o-xylene and butadiene; and U.S. Pat. No. 3,336,411, patented Aug. 15, 1967 to Benham, which teaches isomerization of dimethylnaphthalenes using silica-alumina and other catalysts, and the application of Ronald I. Davis, Ser. No. 263,370, titled "Separation of Xylenes by Adsorption on Partially Dehydrated Copper Zeolites," filed June 6, 1972 (now U.S. Pat. No. 3,793,386 issued Feb. 19, 1974). All of the above-referred to patents and applications are hereby incorporated herein.

BACKGROUND OF THE INVENTION

Molecular sieves have been used to separate distinct classes of organic compounds and have also been used to separate compounds within a given class. The separation of n-paraffins from branched paraffins with 5A molecular sieves is well known. Selective adsorption of aromatics from mixed streams with 10X and 13X sieves is also known. The use of 10X molecular sieves to separate mixtures of aromatics has been disclosed in U.S. Pat. No. 3,114,782 issued Dec. 17, 1963 to Fleck et al. and U.S. Pat. No. 3,133,126 issued May 12, 1964 to Fleck et al. These patents disclose separations of mixtures of monocyclic aromatics and separation of mixtures of dicyclic aromatics. U.S. Pat. No. 3,558,732 issued Jan. 26, 1971, U.S. Pat. No. 3,626,020 issued Dec. 7, 1971 to Neuzil, and U.S. Pat. No. 3,665,046 issued May 23, 1972 to De Rosset, deal with the use of Type X and Y zeolites for separation of a $C_8$ aromatic isomer (e.g., p-xylene) from mixtures of such isomers.

None of the above cited patents disclose that the water content of the zeolite (which depends on the conditions of the dehydration or activation process) can be critical in determining selectivity of the adsorbent.

BRIEF DESCRIPTION OF THE INVENTION

Selective adsorption of one cyclic hydrocarbon from a fluid mixture with a structurally similar cyclic hydrocarbon can be obtained with molecular sieves (crystalline alumino-silicate zeolites) which have been partially dehydrated at a temperature in the range of 80°–300°C. Preferably the Al/Si ratio in the zeolite framework is in the range of 0.2–0.65, for example, p-xylene can be separated from m-xylene by selective adsorption of the p-xylene on NaY zeolite which was partially dehydrated at 125°C. and contains about 12 wt % water by ignition analysis.

A process for separating two structurally similar cyclic hydrocarbons comprises contacting a fluid feed mixture comprising said cyclic hydrocarbons with a solid adsorbant comprising a partially dehydrated, substantially crystalline alumino-silicate zeolite having a critical pore diameter greater than about 6A, the ratio Al/Si of the alumino-silicate framework of the zeolite being in the range of 0.65–0.2, the zeolite having been partially dehydrated by exposure to a temperature in the range of 80°–300°C., whereby there is obtained a rich adsorbent containing an adsorbate which is richer in one said cyclic hydrocarbon than was said fluid feed mixture, and a raffinate product which contains less of the one said cyclic hydrocarbon than did said fluid feed mixture; separating said raffinate product from said rich adsorbent and removing the one said cyclic hydrocarbon from said rich adsorbent.

Good separations of mixtures of cyclic hydrocarbons (e.g., aromatic compounds) of similar structure can be achieved, by preferential adsorption of one component of the mixture, utilizing an adsorbent comprising a crystalline alumino-silicate zeolite having a critical pore diameter greater than about 6A preferably 6.5 to 15A, and wherein the chemical formula of the zeolite can be expressed as $M_x(AlO_2)_x(SiO_2)_y.(H_2O)_z$, where $x$, $y$ and $z$ are integers, the ratio $x:y$ being from 0.65 to 0.2 and where M represents sufficient cations (including $H^+$) of metals, metal oxides or metal hydroxides to balance the electronegativity associated with the alumino-silicate framework of the zeolite. $z$ is preferably greater than $x$, more preferred in the range of $2x$–$8x$, typically $3$–$6x$.

Separation of the eutectic mixture comprising 1,5-dimethylnaphthalene (1,5-DMN) and 2,6-dimethylnaphthalene (2,6-DMN) can be achieved by using the present invention. For example, as described in my application filed May 25, 1972, selective adsorption of 2,6-dimethylnaphthalene from a dimethylnaphthalene concentrate is obtained with Type L molecular sieves which can have an Al/Si ration in the range of 0.2–0.35. Selective adsorption of 1,5-DMN from 2,6-DMN is obtained with a zeolite having an Al/Si ratio in the range of 0.35–0.65 (e.g., Tupe Y), preferably with a faujasite framework. A complex mixture containing the DMN isomers (such as 1,6-DMN) can be utilized instead of a pure binary eutectic mixture.

My application Ser. No. 7,273 (now U.S. Pat. No. 3,668,267) discloses the absorptive separation of cyclic compounds, such as the eutectic mixture of 2,7-dimethylnaphthalene (2,7-DMN) and 2,6-dimethylnaphthalene (2,6-DMN). For example, selective adsorption of 2,7-dimethylnaphthalene from a dimethylnaphthalene concentrate is obtained with sodium Type Y molecular sieves. 2,6-dimethylnaphthalene can then be crystallized from the unadsorbed raffinate fraction. Separation factors of 6 to 8 can be obtained indicating the unexpected high selectivity of these particular molecular sieves (which have an Al/Si atomic ratio in the range of 0.65–0.35, typically 0.5) for this adsorption (especially compared to Type X zeolite).

A continuous method was disclosed in U.S. Pat. No. 3,668,267 for adsorption and desorption of 2,7-dimethylnaphthalene utilizing Type Y zeolites. Type L zeolites, (which have an Al/Si ratio in the range of 0.35–0.2), were disclosed for adsorption and desorption of 2,6-DMN from 2,7-DMN. Compared with 10-X zeolite, Na-Y zeolite was disclosed as having greatly improved selectivity for 2,7-DMN adsorption. A second unexpected discovery was that a much sharper separation was obtained when a mixed refinery stream containing liquid DMN isomers was utilized instead of a pure binary mixture. Also disclosed therein was the unexpected discovery that careful control of water content of the sieve allows improved selectivity.

Also disclosed in U.S. Pat. No. 3,668,267 was the selective adsorption of p-xylene on sodium Y zeolite from a mixture with m-xylene, where the zeolite contained 12 wt. % water.

In general, in the present process selectivity can be improved by controlling the water content of the zeolite (as by the activation procedure, see the applications of Kirsch et al) and/or by choice of the types and relative amounts of metal cations and protons which are in exchange positions on the zeolite. Among the preferred cations are the alkali metals (e.g., $Na^+$, $X^+$) and the rare earths (e.g., $Ce^{+3}$, $La^{+3}$). Partially cation deficient (e.g., protonated) zeolites are also preferred (e.g. CeHY, see Ser. No. 211,040).

FURTHER DESCRIPTION

The said U.S. Pat. No. 3,668,267 contains an equilibrium diagram, the solid curve of which shows the degree to which 2,7-DMN can be removed from its binary eutectic with 2,6-DMN. A second equilibrium diagram shows the degree to which 2,7-DMN can be removed from a "heart-cut" distillate fraction from an aromatic extract obtained by furfural extraction of catalytic gas oil. Two other figures show the "break through" of 2,7-DMN into raffinate (at pump rates of 8 ml./min. and 4 ml./min., respectively) for three desorbents (benzene, ortho-xylene and toluene). Toluene was disclosed as an especially preferred desorbent and is also especially preferred as a desorbent in the present process.

Another figure in that patent is a schematic diagram of a process wherein a selective adsorbent is used for separation of an eutectic mixture of 2,6-DMN and 2,7-DMN (which can be present in admixture with other DMN isomers) into a fraction enriched in 2,6-DMN and a fraction enriched in 2,7-DMN. By syncronizing the operation of the 3 columns, 2,6-DMN enriched streams can be produced in a continuous manner. In effect, at any given point in time, one column will be eluting raffinate which is rich in 2,6-DMN, one column will be eluting a recycle stream, and one column will be eluting a desorbate which is rich in 2,7-DMN. My application filed May 25, 1972 discloses a similar process for separation of 2,6-DMN from 1,5-DMN.

Another figure in the patent is a schematic diagram of a process for obtaining substantially pure 2,7-DMN and substantially pure 2,6-DMN from mixtures, such as an aromatic extract from catalytic gas oil, utilizing a molecular sieve adsorbent. This general process is useful for separation of many types of mixtures of cyclic (including polycyclic) hydrocarbons and, particularly, can be used to obtain substantially pure 2,6-DMN and 2,7-DMN from a wide variety of hydrocarbon streams (such as the bottoms from "ultrafining" (e.g., severe reforming of high boiling naphtha).

My application Ser. No. 207,870 and the application filed May 25, 1972 contain figures showing how isomerization processes can be combined with zeolite adsorption and crystallization. Ser. No. 207,870 also contains a typical plot of catalyst activation (e.g., dehydration) temperature (°C.) versus time and shows that there are temperature "plateaus" in such activations. For example, the plot in Ser. No. 207,870 is for dehydration of a fully hydrated Type Y zeolite and shows that at atmospheric pressure there is one temperature plateau in the range of 100°–150°C (about 125°C.) and a second plateau in the range of 225°–275°C. (about 250°C.). A preferred adsorbent for the present process is one which has been partially dehydrated at at least one such plateau and below 300°C. The pressure in the dehydration can be below atmospheric (e.g., vacuum pump).

In general, procedures shown in these figures can be modified, by the man skilled in the refining art, to enable the separation of other cyclic hydrocarbons.

ILLUSTRATIVE EXAMPLES

Example 1

Several molecular sieves were tested for the separation of 2,6-DMN from 2,7-DMN in the presence of liquid isomers present in a 257-265°C. heart-cut of an aromatic extract of catalytic gas oil. This heart-cut contains:
  12.5% 2,6-DMN (free 2,6-DMN removed)
  16.9% 2,7-DMN
  43.1% Other DMN's
  6.3% 1- and 2-Ethylnaphthalenes
  0.5% Biphenyl
  20.7% Saturates and monocyclic aromatics Prior to evaluation each sieve was carefully conditioned in moist air (about 125°C.) to control the water content of the sieve. Batch adsorptions were then run in which 10.0 g. of heart-cut, 2.5 g. iso-octane, and 5.0 g. of sieve were held at 100°C. for 2 hours to insure complete equilibration between the raffinate and the adsorbate. This 100°C. temperature was chosen because runs at ambient temperature were considerably slower in reaching equilibrium. The unadsorbed (raffinate) fraction was then filtered off and the cooled sieve washed with room temperature iso-octane to remove the remainder of the unadsorbed fraction. The adsorbate was removed with re-fluxing benzene. The results of these evaluations are shown in Table 1. These results show that Sodium-Y sieve is the most selective sieve studied for adsorption of 2,7-DMN, as shown by separation factor, $\alpha$. Where $$\alpha = \frac{\%2,7\text{-}DMN \text{ adsorbed}/\%2,7\text{-}DMN \text{ unadsorbed}}{\%2,6\text{-}DMN \text{ adsorbed}/\%2,6\text{-}DMN \text{ unadsorbed}}$$

Further examination of the data shown in Table 1 reveals several interesting points. Sieve geometry affects selectivity somewhat as shown by the slight differences between powdered, 20–40 mesh size, and tableted Na-Y sieve. Surprisingly, both basic sodium-Y and ammonium-Y sieves and acidic rare earth-Y sieves show selectivity for 2,7-DMN.

A most surprising discovery is that Type L sieve adsorbs 2,6-DMN in preference to 2,7-DMN, the reverse of all other sieves shown in Table 1.

Note also that partial dehydration of the zeolite at temperatures in the range of 100°–230°C. was of use in these separations.

selective. This finding implies that water present in sieves is structural and does affect sieve properties. Sieves with high water contents, up to 25 wt.%, have Table I BATCH RUNS, SELECTIVITY OF VARIOUS MOLECULAR SIEVES FOR SEPARATION OF 2,6-DMN AND 2,7-DMN IN PRESENCE OF 257–265°C. HEART-CUT ISOMERS, 100°C., 2 HRS.

| Type of Sieve | Sieve Pretreatment Temperature in Air (°C.) | Sieve Capacity (g. Hydrocarbon/ 100 g. Sieve) | Separation Factor, $\alpha$ |
|---|---|---|---|
| Sodium form, Type Y, powder (SK-40) | 125 | 16.6 | 8.0 |
| Sodium form, Type Y, 20–40 mesh** | 125 | 11.4 | 7.3 |
| Sodium form, Type Y, tablet | 125 | 15.0 | 6.5 |
| Ammonium form, Type Y, powder | 125 | 13.2 | 5.8 |
| Rare earth exchanged, Type Y, pellet (SK-500) | 125 | 11.8 | 4.7 |
| Sodium form, Type Y, 1/16" extrudate | 125 | 13.6 | 4.4 |
| Linde 13-X 14×30 mesh | 125 | 9.2 | 2.8 |
| Linde 10-X 1/16" extrudate | 100 | 6.6 | 2.4 |
| Potassium form, Type L (SK-45) | 125 | 11.4 | 0.53 |
| Cerium form, Type Y, powder*** | 230 | 21.6 | 5.6 |

*2,6-DMN preferentially adsorbed.
**1/16" extrudate ground to 20–40 mesh.
***Prepared NHy-exchanged Na Y which was then exchanged with cerium nitrate, washed, dryed and calcined at 390°C. before pretreatment in air (see United States Serial No. 716,190, filed March 26, 1968, of Kirsch et. al. for details of exchange and calcination).

EXAMPLE II

Intuitively, one would predict that separation of a binary mixture should be simpler than separation of two components present in a complex mixture. Surprisingly, as shown in Table II, a much higher separation factor is obtained with a mixed stream than with a binary eutectic. Despite the dilution of 2,7-DMN present in adsorbate by liquid isomers, the weight 2,7-DMN freed per 100g. sieve drops only slightly. This enhanced separation is further illustrated by the equilibrium diagrams for the binary eutectic (FIG. 1) and for the heart-cut mixture (FIG. 2).

reduced capacity for dinuclear aromatics. Sieves wet with methanol have greatly reduced selectivity; conditioning of methanol-wet sieves in moist air at 125°C. restores original selectivity.

In continuous commercial scale operation over long time periods the water content of the zeolite may become less than optimum (due to water removal, as will the desorbate). Therefore, samples of the zeolite adsorbent should be analyzed from time to time and the moisture content of the bed adjusted (as by steam injection or by passing moist air through the bed or by adding controlled amounts of water to the feed stock and/or desorbent). In the event that the water content Table II BATCH RUNS, COMPARISON OF PURIFIED BINARY EUTECTIC VS. 257–265°C. HEART-CUT MIXTURE, 100°C., 2 HRS.

| Charge Stock | Type of Sieve | Adsorbed Phase % 2,6-DMN | Adsorbed Phase % 2,7-DMN | Separation Factor, $\alpha$ | Wt. 2,7-DMN Freed/ 100 g. Sieve |
|---|---|---|---|---|---|
| Purified Eutectic | Sodium form, Type Y, powder | 23.7 | 76.3 | 3.1 | 5.8 |
| Heart-Cut Mixture | Sodium form, Type Y, powder | 4.4 | 38.0 | 8.0 | 5.2 |
| Purified Eutectic | Sodium form, Type Y, tablet | 28.8 | 71.2 | 2.8 | 4.8 |
| Heart-Cut Mixture | Sodium form, Type Y, tablet | 4.8 | 37.0 | 6.8 | 4.4 |

EXAMPLE III

Control of water content of the molecular sieve adsorbent is quite important. An optimum $H_2O$ content of 12.0% for Na-Y sieve is shown in Table III. This water content was determined by weight loss on ignition at 1900°F. Sieves having lower water contents are less of the bed is greater than optimum, dry air or a hot dry hydrocarbon can be passed through the bed. If the sieve capacity or selectivity is caused to decrease due to adsorption of impurities in the feed or desorbent, the sieve can be regenerated by calcining or burning, followed by moist air to adjust the water content.

Table III

BATCH RUNS, EFFECT OF WATER CONTENT ON MOLECULAR SIEVE SELECTIVITY IN ADSORPTION OF 2,7-DMN FROM 257–265°C. HEART-CUT ISOMERS 100°C., 2 HRS.

| Type of Sieve | Sieve Pretreatment Temperature in Air (°C.) | Wt. % HO* | Sieve Capacity (g./100g. Sieve) | Separation Factor, $\alpha$ |
|---|---|---|---|---|
| Sodium form, Type Y, powder | 125 | 12.00 | 16.6 | 8.0 |
| Sodium form, Type Y, powder | 400 | 2.30 | 20.6 | 3.2 |
| Sodium form, Type Y, tablet | 25 | 23.34 | 4.4 | 4.1 |
| Sodium form, Type Y, tablet | 125 | 12.13 | 15.0 | 6.5 |
| Sodium form, Type Y, tablet | 175 | 6.00 | 21.2 | 5.2 |
| Sodium form, Type Y, tablet | Methanol washed | 10.02 | 15.0 | 3.5 |

*Based on weight of conditioned sieve.

EXAMPLE IV

To develop a cyclic separation process a suitable desorbent must be found. A suitable desorbent must allow selective adsorption and yet must desorb at a reasonable rate. In this example, three aromatic desorbents were evaluated: benzene, toluene, and o-xylene.

Batch competition experiments with equal weights of desorbent and DMN heart-cut were run to determine the effect of desorbent on selectivity for adsorption of 2,7-DMN over 2,6-DMN. The relative strength with which desorbent or any other component of a mixture is adsorbed can be shown by $\beta$ factor. $\beta$ factor is defined as the ratio of component $x$ in the adsorbed phase over component phase over component $x$ in the unadsorbed phase divided by wt. 2,6-DMN adsorbed over wt. 2,6-DMN unadsorbed. The $\beta$ factor for 2,7-DMN is equal to $\alpha$ as defined earlier.

$$\beta \text{ factor for component } x = \frac{\text{Wt. } x \text{ adsorbed/Wt. } x \text{ unadsorbed}}{\text{Wt. 2,6-}DMN \text{ adsorbed/Wt. 2,6-}DMN \text{ unadsorbed}}$$

The results of competition studies are shown in Table IV. The most selective adsorption of 2,7-DMN occurs in the presence of o-xylene, the most weakly adsorbed desorbent. The least selective adsorption occurs in the presence of benzene, the most strongly adsorbed desorbent. It is quite interesting to see that other DMN isomers are adsorbed more strongly than 2,6-DMN. This may explain why the higher separation factors were obtained with the heart-cut mixture.

Table IV

COMPETITION OF BENZENE, TOLUENE, AND O-XYLENE WITH DIMETHYLNAPHTHALENES FOR ADSORPTION ON MOLECULAR SIEVE, $\beta$ FACTORS OBTAINED FROM BATCH STUDIES
(Factor 2,6-DMN chosen equal to 1.0)

|  | Benzene | Toluene | o-Xylene |
|---|---|---|---|
| 2,7-DMN | 2.7 | 4.7 | 8.0 |
| Other DMN's | 2.0 | 2.2 | 2.3 |
| Benzene | 1.8 | — | — |
| 1,6-DMN | 1.4 | — | 1.9 |
| 1- and 2-Ethylnapthalenes | 1.7 | 1.8 | 1.8 |
| 2,6-DMN | 1.0 | 1.0 | 1.0 |
| Toluene | — | 0.9 | — |
| o-xylene | — | — | 0.7 |
| Mixed Monocyclic Aromatics | 0.6 | 0.6 | 0.6 |

These batch competition studies show that benzene caused the fastest desorption while o-xylene would allow the sharpest separation. In view of this dilemma, all three desorbents were investigated in column studies.

EXAMPLE V

The experimental apparatus used for column studies consisted of ¾ in. I.D. by 36 in. glass column filled with Na-Y sieve containing about 12 wt.% water (by ignition analysis). At the start of each run the column is filled with desorbent. The DMN heart-cut containing eutectic 2,6-DMN and 2,7-DMN is pumped into the bottom of the column. At the end of this DMN charge, desorbent is pumped into the bottom of the column. The desorbent pushes out a 2,6-DMN enriched raffinate and desorbs the 2,7-DMN enriched adsorbate. When the last of the adsorbate is removed from the bottom portion of the sieve bed, the column is ready for a new cycle. The incoming DMN feed pushes out the remainder of the 2,7-DMN enriched desorbate. The effluent from the column was taken in small cuts for the initial studies. These cuts were then analyzed by gas chromatography.

The adsorbent column is held at a temperature just below the boiling point of the desorbent in order to speed diffusion into the sieve particles.

The column runs showed that, as in the batch study, benzene is the most efficient stripping solvent. o-xylene was quite slow to desorb 2,7-DMN and is not preferred in any industrial scale cyclic process.

Sharpness of separation is shown by plotting the breakthrough curve of 2,7-DMN into the raffinate. Breakthrough curves for these three desorbents are shown in FIG. 3. Benzene allows a rapid breakthrough of 2,7-DMN. Surprisingly, toluene is superior to o-xylene at the 8.0 ml/min pump rate shown in FIG. 3. At a slower 4.0 ml/min pump rate the curves for toluene and o-xylene are superimposable (FIG. 4). Toluene allows faster equilbration than o-xylene and thus toluene is superior at higher flow rates. Therefore, toluene is the preferred desorbent for a commercial scale separation process.

EXAMPLE VI

A separation process can be effected using three synchronized molecular sieve columns. At a given point in time one column is eluting 2,6-DMN enriched raffinate, the second column is eluting poorly separated charge to be recycled, and the third column is undergoing desorption of 2,7-DMN enriched adsorbate.

A more efficient, commercial scale process involves the apparatus and techniques used in the Molex process.

Similarly, crystalline alumino-silicate zeolites wherein the atomic ratio Al/Si in the zeolite framework is in the range of 0.65 to 0.2 (e.g., Y and L zeolites) can be used to separate other structurally similar polycyclic hydrocarbons such as octahydroanthracene from octahydrophenanthrene and fluorene from 5,6-benzindan.

EXAMPLE VII 5.0g of a mixture containing:
69.0 wt.% fluorene
20.7 wt.% 5,6-benzindan
11.3 wt.% other aromatics
was dissolved in 25 ml. iso-octane and the resulting solution was contacted for 2 hrs. at 100°C. with 10.0g. sodium-Y molecular sieve containing about 12 wt.% water (by ignition analysis). The raffinate fraction (3.51g.) contained 66.0 wt.% fluorene and 24.0 wt.% 5,6-benzindan. The adsorbed fraction (1.49g) was enriched in fluorene (77.5 wt.%) and low in 5,6-benzindan (10.9%). The separation factor was 2.60. Since fluorene and 5,6-benzindan form a series of solid solutions, this separation is superior to crystallization.

EXAMPLE VIII 10.0g. of a eutectic mixture of 20 wt.% s-octahydroanthracene (OHA) and 80 wt.% s-octahydrophenanthrene (OHP) was dissolved in 25 ml. iso-octane and the resulting solution was contacted for 2 hours at 100°C. with sodium-Y molecular sieve (containing 12 wt.% water). The raffinate (8.52g.) contained 72.7% OHP and 27.3% OHA. The adsorbate fraction (1.48g. desorbed with refluxing benzene) contained 93.7% OHP and 8.3% OHA. The separation factor was 5.6. Thus, OHP is selectively adsorbed.

EXAMPLE IX 10g. of a mixture of 46.2 wt.% anthracene and 53.8% phenanthrene was dissolved in 50 ml. of iso-octane and 75 ml. of toluene. The resulting solution was contacted with 10g. sodium-Y molecular sieve (containing 12 wt.% water by ignition analysis) for 2 hours at 100°C. The raffinate fraction (9.51g.) was 56.5% anthracene and 43.4% phenanthrene. The adsorbed fraction (removed by refluxing benzene) was enriched in phenanthrene (74.9 wt.%) and decreased in anthracene (25.1 wt.%). The separation factor was 3.9.

EXAMPLE X 10g. of a mixture of 50 wt.% acenaphthene and 50 wt.% 2,3-dimethylnaphthalene (2,3-DMN) in 10g. iso-octane was contacted with 10g. of sodium-Y molecular sieve (containing 12% water by ignition test) for 2 hours at 100°C. The raffinate (3.24g.) contained 49.6% acenaphthene and 50.4% 2,3-DMN. The adsorbate (1.76g., removed by refluxing benzene) was enriched in acenaphthene (58.8%) and decreased in 2,3-DMN (41.2%). The separation factor was 1.5.

EXAMPLE XI

This example and Example XII show that separations of mixtures of monocyclic aromatics are relatively poor with sodium-Y molecular sieves as the adsorbent.

A solution of 2.5g. p-xylene and 2.5g. m-xylene in 5.0g. iso-octane was contacted with 10.0g. sodium-Y molecular sieve (containing 12 wt.% water by ignition analysis) for 3 hours at 75°C. p-xylene was preferrentially adsorbed with a 1.14 separation factor.

It should be noted that 10-X sieves have been reported to adsorb m-xylene in preference to p-xylene (see Example I, R. N. Fleck and C. G. Wright, U.S. Pat. No. 3,114,782, issued Dec. 17, 1963, to Union Oil of California).

In this example the zeolite was activated by partial dehydration for 4 days in an air oven at 125°C.

EXAMPLE XII

A mixture of 5.0g. benzene and 5.0g. toluene was contacted with sodium-Y molecular sieve (containing 12 wt.% water by ignition analysis) for 1 hour at 62°C.

Equilibration was complete at this point. Benzene was adsorbed in preference to toluene, the separation factor being 1.59.

Note that toluene has been reported to be adsorbed on hydrogen Y-zeolite in preference to benzene (P. B. Venuto, E. L. Wu, and V. Cattanach, Preprints, Society of Chemical Industry, London, 1967).

EXAMPLE XII

Structurally similar naphthenic hydrocarbons can be separated by selective adsorption on zeolites wherein the ratio Al/Si of the zeolite framework is in the range of 0.65–0.2 and the critical pore diameter is in the range of 6–15A.

An eutectic mixture of 2.35g. trans, syn -2- syn -6- dimethyldecalin and 7.65g. trans, syn -2- syn -7- dimethyldecalin was contacted with 10.0g. sodium-Y molecular sieve (12 wt.% water) at 100°C. for 2 hours. The raffinate fraction (9.3g.) contained 76.1% 2,7-dimethyldecalin and 23.9% 2,6-dimethyldecalin. Adsorbate fraction (0.70g.) contained 81.1% 2,7-dimethyldecalin and 18.9% 2,6-dimethyldecalin (separation factor 1.34). It should be noted that the weight of this adsorbate fraction was only 0.7g. or 7g. per 100g. of sieve, which is much lower than the capacity of sodium-Y sieves for dimethylnaphthalenes.

The separation of 2,6-dimethyldecalin and 2,7-dimethyldecalin eutectic via trans 2,6-dimethyldecalin crystallization and the properties of eutectic mixtures of trans-syn-2-syn-6 with trans-syn-2-syn-7-dimethyldecalin are disclosed in copending application Ser. No. 779,827, of John A. Hedge, filed Nov. 29, 1968, now U.S. Pat. No. 3,541,175 issued Nov. 15, 1970. The disclosure of Ser. No. 779,827 is hereby incorporated herein by reference.

EXAMPLE XIII

All of the previous examples have been of liquid phase adsorption. Vapor phase adsorption can also be used to separate structurally similar polycyclic hydrocarbons, for example, 2,6-DMN from 2,7-DMN.

11.1g. of sodium-Y sieve (containing 12 wt. $H_2O$) was heated slowly to 300°C., well above the 257°–265°C. boiling range of a dinuclear aromatic extract containing 2,6- and 2,7-DMN's. Water was driven off this sieve (thus, reducing selectivity) until the sieve had a weight loss on ignition (at 1900°F.) of about 4%. Dinuclear extract (4.1g.) was charged to the 300°C. sodium Y-zeolite column in 1.5 min. The unadsorbed fraction (2.66g.) contained 15.8% 2,6-DMN and 16.6% 2,7-DMN. The adsorbed fraction was removed by flushing with 4 – 10cc. volumes of benzene which were collected and analyzed individually (see Table V). A separation factor of 2.6 was achieved.

Table V

VAPOR PHASE SEPARATION OF 2,6-DMN FROM 2,7-DMN IN PRESENCE OF 257–265°C. HEART-CUT ISOMERS, DESORPTION OF 2,7-DMN ENRICHED ADSORBATE WITH BENZENE AT 300°C.

| Desorbed Fractions | % 2,6-DMN | % 2,7-DMN | Wt. Extract Recovered (g.) |
|---|---|---|---|
| First 10cc. Benzene | 9.2 | 21.3 | .91 |
| Second 10cc. Benzene | 4.7 | 19.9 | .25 |
| Third 10cc. Benzene | 3.8 | 17.5 | .13 |
| Fourth 10cc. Benzene | 3.3 | 15.6 | .13 |
| Average Adsorbed Fraction | 7.3 | 20.1 | 1.42g. |

The large volume of desorbent required to remove the 2,7-DMN makes vapor phase separation unattractive in comparison with liquid phase separation. However, pressure-sweep cycles (e.g. alternating high and low pressures) can be used (particularly in conjunction with a more polar desorbant, as ammonia or organic amines) to improve the desorption step.

The process disclosed herein can also be used to separate other chemically similar cyclic and polycyclic compounds (which can be carbocyclic or heterocyclic), especially oxygenated (e.g., estus, acids, ethers, alcohols), halogenated (e.g. chlorinated), or nitiogenated (e.g. amenes, amides, nitro compounds) cyclic and polycyclic compounds. Branched, cyclic olefins, such as terpenes or methyl substituted cyclopentadiene can also be separated by the disclosed process as can alpha-methyl naphthalene from beta methyl naphthalene.

In general, it is preferred that the cyclic or polycyclic hydrocarbons have a critical diameter (or a substituent group, e.g., methyl, ethyl) no greater than that of the zeolite, although in some cases molecules of larger critical diameter can be separated due to differences in polarity. The preferred polycyclic hydrocarbons contain from 2-6 condensed rings with the total number of ring carbon atoms being in the range of 9-25. The critical pore diameter of a zeolite can be determined by the "plug-gauging," e.g., see U.S. Pat. No. 3,130,006, to Breck, issued Apr. 14, 1958 and Barrer, R. M., Quarterly Review III, 301 (1949).

EXAMPLE XIV

Example XI was repeated except that the molecular sieve was a rare-earth exchanged sodium Y zeolite (available commercially as "Linde SK-500" from Union Carbide Corporation) and was partially dehydrated at 450°C. to produce an adsorbent having a loss on ignition at 1900°F. of 3.5 wt.%. The zeolite was selective for m-xylene with a separation factor of 1.04.

EXAMPLE XV

Example XI was repeated except that the molecular sieve was hydrogen mordenite, (available from Norton Co.) and the partial dehydration was at 125°C. The zeolite was selective for p-xylene with a separation factor of 1.58.

Other zeolites (including acid-leached mordenites) which can be used for separations of cyclic hydrocarbons include those described in Ser. No. 28,608 filed Apr. 15, 1970, Ser. No. 90,463 filed Nov. 17, 1970 and Ser. No. 185,615 filed Oct. 1, 1971, all of Hirschler, the disclosure of which are hereby incorporated herein by reference.

EXAMPLE XVI

A mixture was obtained from isomerization of 1,5-DMN with HF catalyst. The mixture had the following analysis
4.0 % Lower boiling aromatics
8.1 % 2,6-DMN
31.2 % 1,6-DMN
54.8 % 1,5-DMN
0.5 % 2,7-DMN
1.4 % Higher Boiling aromatics 10 g. of the mixture and 10 g. iso-octane were heated to 100°C. Then 10 g. NaY sieve (14 x 30 mesh) which had been dried at 125°C., was added with stirring. The slurry was maintained at 100°C. for 1 hour with stirring. Then a raffinate was removed by filtration and the sieve was washed with room temperature iso-octane, and the wash plus filtrate were combined as the unadsorbed fraction. The adsorbed fraction was desorbed from the sieve with hot benzene and finally with hot methanol, and the products combined as the adsorbed fraction. The analysis of the fractions follows:

|  | Lower Boiling | 2,6-DMN | 2,7-DMN | 1,6-DMN | 1,5-DMN | Higher Boiling | Wt. g. |
|---|---|---|---|---|---|---|---|
| Unadsorbed | 4.3 | 9.1 | — | 31.2 | 53.7 | 1.7 | 9.09 |
| Adsorbed | 3.8 | 3.3 | 5.7 | 15.8 | 70.3 | 1.1 | .91 |
|  |  |  |  |  |  |  | 10 g |

α 1,5-DMN/2,6-DMN = 3.61

Also note that the adsorbent selectively removed traces of 2,7-DMN present as an impurity.

The invention claimed is:
1. A process for separating two structurally similar cyclic hydrocarbons selected from the group consisting of benzene, toluene and xylenes, said process comprising:
  A. contacting a fluid feed mixture comprising said cyclic hydrocarbons with a solid adsorbent comprising a partially dehydrated, substantially crystalline alumino-silicate sodium Y zeolite having a critical pore diameter greater than about 6A, the ratio Al/Si of the alumino-silicate framework of the zeolite being in the range of 0.65–0.2, the zeolite having been partially dehydrated to a water content of 6–20 weight percent exposure to a temperature in the range of 80°–300°C., whereby there is obtained a rich adsorbent containing an adsorbate which is richer in one said cyclic hydrocarbon than was said fluid feed mixture, and a raffinate product which contains less of the one said cyclic hydrocarbon than did said fluid feed mixture;
  B. separating said raffinate product from said rich adsorbent and,
  C. removing the one said cyclic hydrocarbon from said rich adsorbent.
2. Process according to claim 1 wherein said substantially crystalline alumino-silicate zeolite is at least 50% crystalline by X-ray, compared to a fully hydrated pure specimen of said zeolite, and wherein there is a loss of 8–18% weight percent water upon ignition analysis of said zeolite at 1900°F.
3. Process according to claim 1 wherein said loss of water upon ignition analysis is about 12 weight percent and wherein the said ratio Al/Si is in the range of 0.35–0.65.
4. Process according to claim 1 wherein p-xylene is separated from m-xylene by preferential adsorption of said p-xylene.
5. Process according to claim 1 wherein said zeolite has been partially dehydrated at a temperature in the range of 125°–175°C.

* * * * *